(12) United States Patent
Kanayama et al.

(10) Patent No.: US 7,601,807 B2
(45) Date of Patent: Oct. 13, 2009

(54) PROTEASE, DNA ENCODING THE SAME, AND METHOD FOR MANUFACTURING PROTEASE

(75) Inventors: Yoshitaka Kanayama, Sendai (JP); Yasuo Sakai, Sendai (JP); Takahiro Hongo, Sendai (JP)

(73) Assignee: Jellice Co., Ltd., Sendai-shi (JP)

( * ) Notice: Subject to any disclaimer, the term of this patent is extended or adjusted under 35 U.S.C. 154(b) by 0 days.

(21) Appl. No.: 11/287,307

(22) Filed: Nov. 28, 2005

(65) Prior Publication Data

US 2006/0134749 A1    Jun. 22, 2006

Related U.S. Application Data

(63) Continuation of application No. PCT/JP2004/007419, filed on May 24, 2004.

(30) Foreign Application Priority Data

May 27, 2003    (JP)    ............................. 2003-148886

(51) Int. Cl.
*C07K 1/00*    (2006.01)
(52) U.S. Cl. ...................... 530/350; 530/300; 435/69.1; 435/6; 435/320.1; 435/325; 435/252
(58) Field of Classification Search ........................ None
See application file for complete search history.

(56) References Cited

FOREIGN PATENT DOCUMENTS

| JP | 07-067639 | 3/1995 |
|---|---|---|
| JP | 08-266276 | 10/1996 |
| JP | 2000-102381 | 4/2000 |
| JP | 2000-325095 | 11/2000 |
| WO | WO 2004/033668 A2 | 4/2004 |

OTHER PUBLICATIONS

Seffernick et al. (J. Bacteriology, vol. 183, pp. 2405-2410, 2001).*
Wells, Biochemistry, vol. 29, pp. 8509-8517, 1990.*
Lecroisey et al, FEBS Letters, (1975), vol. 59, No. 2, pp. 167-172.
Kabashima et al, Biochimica et Biophysica. Acta., (1999), vol. 1429, pp. 516-520.
Ogasawara et al, Biosci. Biotech. Biochem., (1997), vol. 61, No. 1, pp. 146-151.
Y. Kanayama, et al. "Purification and Properties of a New Type of Protease Produced by Microbacterium liquefaciens" Biosci. Biotechnol. Biochem., 69 (5), pp. 916-921, 2005.

* cited by examiner

*Primary Examiner*—Hope A Robinson
(74) *Attorney, Agent, or Firm*—Oblon, Spivak, McClelland, Maier & Neustadt, L.L.P.

(57) ABSTRACT

A protease having the following characteristics:
(i) a molecular weight of 21,000±1,000 (by SDS-PAGE) and
(ii) specific protease activity cutting the Gly-Phe site of a peptide or protein comprising amino acid sequence (1) below, cutting the Gly-Phe site of a peptide or protein comprising amino acid sequence (2) below, or cutting the Ser-Leu site of a peptide or protein comprising amino acid sequence (3) below:

Pro-Gln-<u>Gly-Phe</u>-Gln-Gly-Pro    (1) (SEQ ID NO:4)

Pro-Ala-<u>Gly-Phe</u>-Ala-Gly-Pro    (2) (SEQ ID NO:5)

Gln-Thr-Gln-<u>Ser-Leu</u>-Val-Thr-Pro.    (3) (SEQ ID NO:6)

DNA encoding this protease, including vectors containing this DNA, and a method for producing this protease by transforming a cell with this DNA.

12 Claims, 1 Drawing Sheet

Figure 1

Electrophoresis of GLD

SDS-PAGE analysis of GLD produced from *Aureobacterium* sp. MIG-CG-9535-I

SEQUENCE LISTING

<160> NUMBER OF SEQ ID NOS: 17

<210> SEQ ID NO 1
<211> LENGTH: 819
<212> TYPE: DNA
<213> ORGANISM: Aureobacterium sp.

<400> SEQUENCE: 1

```
ttgcgactca cgagaaaact ggcgtttcgc gctaccgcgg ctgctgcgct ctgccgcgcc     60
acggtcatcc ccgctgccgc gaattccgca cccgacgccg acgacatccc caccttccag    120
gagttcgagg cgtcgaccta tcgagacatc gacggagcct acgtcgtcaa cggagacgag    180
gtgatctcca atcagggcga gctgcggtcg ttctacgaac agctcctcgg cgccgatccc    240
gtgaccaacg gcctcatcgt caacacggtc aacagcatcg acgacaagtg gtcagacgcg    300
caggcgagcg ccctcaccta ctgcgtcagc acggcattcg gtgcacgtca cgccgacgtc    360
gtgagcgcga tggaaagcgg cgccgcgctc tgggaggccg catcatcgaa gatcgacttc    420
atctacgaca gcagcgccga cgccaactgc acgacgcgca acaacgccgt cctcttctcc    480
gtggagcccg tgcagacgac gcagtacatc gcccgggcct tcttcccgag cacggcgccg    540
cgcctgcaga acgtcctcat cgacgactcg atctggaccc cgggctcgtc ctggaccccg    600
acgaatgtgc tgggtcatga gctcggccac gtgctcggct ccgccacgga gcacacccgc    660
cccgaggccg gcacctgctt cgaggacgac aactggcgtc cgctgacgcc gtatgactcg    720
tcgtcgatca tgcactaccc gcagtgcaac ggatcgtccg ccgatctgtc gatgacgagc    780
gtcgacaccg acggagtcgt cgcactctac ggaaactga                           819
```

<210> SEQ ID NO 2
<211> LENGTH: 272
<212> TYPE: PRT
<213> ORGANISM: Aureobacterium sp.

<400> SEQUENCE: 2

```
Met Arg Leu Thr Arg Lys Leu Ala Phe Arg Ala Thr Ala Ala Ala Ala
1               5                   10                  15

Leu Cys Leu Gly Thr Val Ile Pro Ala Ala Ala Asn Ser Ala Pro Asp
            20                  25                  30

Ala Asp Asp Ile Phe Thr Phe Gln Glu Phe Glu Ala Ser Thr Tyr Arg
        35                  40                  45

Asp Ile Asp Gly Ala Tyr Val Val Asn Gly Asp Glu Val Ile Ser Asn
    50                  55                  60

Gln Gly Glu Leu Arg Ser Phe Tyr Glu Gln Leu Leu Gly Ala Asp Pro
65                  70                  75                  80

Val Thr Asn Gly Leu Ile Val Asn Thr Val Asn Ser Ile Asp Asp Lys
                85                  90                  95

Trp Ser Asp Ala Gln Ala Ser Ala Leu Thr Tyr Cys Val Ser Thr Ala
            100                 105                 110

Phe Gly Ala Arg His Ala Asp Val Val Ser Ala Met Glu Ser Gly Ala
        115                 120                 125

Ala Leu Trp Glu Ala Ala Ser Ser Lys Ile Asp Phe Ile Tyr Asp Ser
    130                 135                 140

Ser Ala Asp Ala Asn Cys Thr Thr Arg Asn Asn Ala Val Leu Phe Ser
145                 150                 155                 160

Val Glu Pro Val Gln Thr Thr Gln Tyr Ile Ala Arg Ala Phe Phe Pro
```

```
                    165                 170                 175
Ser Thr Ala Pro Arg Leu Gln Asn Val Leu Ile Asp Asp Ser Ile Trp
                180                 185                 190

Thr Pro Gly Ser Ser Trp Thr Pro Thr Asn Val Leu Gly His Glu Leu
                195                 200                 205

Gly His Val Leu Gly Phe Arg His Glu His Thr Arg Pro Glu Ala Gly
            210                 215                 220

Thr Cys Phe Glu Asp Asp Asn Trp Arg Pro Leu Thr Pro Tyr Asp Ser
225                 230                 235                 240

Ser Ser Ile Met His Tyr Pro Gln Cys Asn Gly Ser Ser Ala Asp Leu
                245                 250                 255

Ser Met Thr Ser Val Asp Thr Asp Gly Val Val Ala Leu Tyr Gly Asn
                260                 265                 270

<210> SEQ ID NO 3
<211> LENGTH: 188
<212> TYPE: PRT
<213> ORGANISM: Aureobacterium sp.

<400> SEQUENCE: 3

Leu Ile Val Asn Thr Val Asn Ser Ile Asp Asp Lys Trp Ser Asp Ala
1               5                   10                  15

Gln Ala Ser Ala Leu Thr Tyr Cys Val Ser Thr Ala Phe Gly Ala Arg
                20                  25                  30

His Ala Asp Val Val Ser Ala Met Glu Ser Gly Ala Ala Leu Trp Glu
            35                  40                  45

Ala Ala Ser Ser Lys Ile Asp Phe Ile Tyr Asp Ser Ser Ala Asp Ala
        50                  55                  60

Asn Cys Thr Thr Arg Asn Asn Ala Val Leu Phe Ser Val Glu Pro Val
65                  70                  75                  80

Gln Thr Thr Gln Tyr Ile Ala Arg Ala Phe Phe Pro Ser Thr Ala Pro
                85                  90                  95

Arg Leu Gln Asn Val Leu Ile Asp Asp Ser Ile Trp Thr Pro Gly Ser
                100                 105                 110

Ser Trp Thr Pro Thr Asn Val Leu Gly His Glu Leu Gly His Val Leu
            115                 120                 125

Gly Phe Arg His Glu His Thr Arg Pro Glu Ala Gly Thr Cys Phe Glu
        130                 135                 140

Asp Asp Asn Trp Arg Pro Leu Thr Pro Tyr Asp Ser Ser Ser Ile Met
145                 150                 155                 160

His Tyr Pro Gln Cys Asn Gly Ser Ser Ala Asp Leu Ser Met Thr Ser
                165                 170                 175

Val Asp Thr Asp Gly Val Val Ala Leu Tyr Gly Asn
            180                 185

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

Pro Gln Gly Phe Gln Gly Pro
1               5

<210> SEQ ID NO 5
```

```
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Pro Ala Gly Phe Ala Gly Pro
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Gln Thr Gln Ser Leu Val Thr Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Pro Gln Gly Ile Ala Gly Gln
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 8

Gly Pro Ala Gly Phe Ala Gly Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Gly Pro Gln Gly Phe Gln Gly Pro
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

Gly Pro Ala Gly Phe Ala Gly
1               5

<210> SEQ ID NO 11
<211> LENGTH: 6
```

```
<212> TYPE: PRT
<213> ORGANISM: Artificial Sequence
<220> FEATURE:
<223> OTHER INFORMATION: Synthetic Peptide

<400> SEQUENCE: 11

Gly Pro Ala Gly Phe Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 12

Gly Pro Ala Gly Phe
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 13

Ala Gly Phe Ala Gly Pro
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 14

Gly Phe Ala Gly Pro
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 15

Gly Pro Gln Gly Phe Gln Gly Pro Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

Gly Pro Ala Gly Phe Ala Gly Pro Lys
1               5

<210> SEQ ID NO 17
<211> LENGTH: 8
<212> TYPE: PRT
```

```
<213> ORGANISM: Artificial Sequence
<220> FEATURE:
<223> OTHER INFORMATION: Synthetic Peptide

<400> SEQUENCE: 17

Thr Gln Ser Leu Val Thr Pro Lys
1               5
```

PROTEASE, DNA ENCODING THE SAME, AND METHOD FOR MANUFACTURING PROTEASE

This application is a continuation of PCT/JP04/007419, filed May 24, 2004 and claims benefit under 119 (a-d) to foreign document JAPAN 2003-148886, filed May 27, 2003.

TECHNICAL FIELD

The present invention relates to a novel protease, DNA comprised of a base sequence encoding this protease, a recombinant vector comprising this DNA, a transformant comprising this recombinant vector, and a method for manufacturing protease employing this transformant.

BACKGROUND ART

Gelatins in the form of heat-denatured collagens are widely employed as gelling agents, foaming agents, thickeners, and the like in foods, cosmetics, and the like. They are also employed for drug capsules. Collagens are fibrous proteins that, together with elastins, constitute animal connective tissue. Their applications include foods, cosmetics, pharmaceuticals, paints, and plastic materials.

Gelatins and collagens generally have molecular weights of roughly 100,000 to 300,000. Digested gelatins and collagens generally have molecular weights of not greater than 10,000.

However, given the various and sundry applications listed above, there is a need for collagens and gelatins having desirable properties such as low antigenicity, high solubility, low gelling strength, the ability to readily form films, and the ability to readily clathrate other molecules. Thus, there is demand for gelatins and collagens with molecular weights other than those stated above.

In the past, proteases and collagenases have been employed to degrade gelatins and collagens to achieve lower molecular weights. It is known that these enzymes can be obtained by cultivating *Achromobacter iophagus* and *Clostridium histolyticum*.

However, there are problems in that these microbes have been determined to be pathogenic and must be cultured under anaerobic conditions. Achieving large quantities of enzyme from these microbes involves complex operations. Further, the enzymes obtained from these microbes end up degrading gelatins and collagens into minimal units (molecular weights of several hundred to several thousand), precluding the obtaining of gelatin and collagen degradation products of suitable molecular weight.

Collagenase from the small intestine is also known. This enzyme is expensive. Obtaining it entails a complex operation, and achieving large-volume production is difficult. Thus, the use of this substance cannot be considered industrially advantageous. Further, this collagenase degrades collagen into a molecular weight of several hundred to several thousand.

Accordingly, the present inventors first conducted extensive investigation with the goal of providing an enzyme for manufacturing degradation products of gelatins and collagens of suitable molecular weight. As the result of extensive exploration of the natural world for enzymes degrading gelatins and collagens into peptides of suitable molecular weight, they discovered in soil a microbe producing an enzyme degrading gelatins and collagens with molecular weights of about 130,000 into peptides with molecular weights of about 70,000 and about 40,000 and submitted a patent application (Japanese Patent Application Publication No. 2000-102381).

The protease described in the above-cited patent application publication comprises the following five properties:

(1) Function

The protease exhibits limited degradation activity by degrading heat-denatured collagens with a molecular weight of about 130,000 and nondenatured soluble collagens of about 300,000 in molecular weight into peptides of about 70,000 and 40,000 in molecular weight, but exhibits only slight degradation activity on the synthetic substrate DNP-Pro-Gln-Gly-Ile-Ala-Gly-Gln-D-Arg, a collagenase substrate, and no degradation activity on the synthetic substrate DNP-Gln-Gly-Ile-Ala-Gly-Gln-D-Arg. Further, it exhibits degradation activity on azocol or casein. Here, DNP denotes a dinitrophenyl group and D denotes the D form of Arg.

(2) Optimal pH:

pH 5.5 to 7

(3) Optimal Temperature:

37 to 40° C.

(4) Molecular Weight 23,000±2,000 (by SDS-PAGE)

(5) Enzyme Inhibition:

Activity is inhibited by o-phenanthroline and L-cysteine, but not by ethylenediamine tetraacetic acid, N-ethylmaleimide, phenylmethanesulfonyl fluoride, or iodoacetamide.

The above protease is manufactured by culturing a protease-producing bacterium of the genus *Microbacterium* and extracting the protease from the culture product. In the above-cited patent application publication, it is disclosed that the above protease is manufactured by culturing a protease-producing bacterium of the genus *Aureobacterium* and extracting the protease from the culture product. However, upon subsequent examination, we have lumped the genus *Aureobacterium* with the genus *Microbacterium*.

As the result of further research, the present inventors discovered that the above culture contained a new protease in addition to the above-stated protease, that this protease had cleavage specificity for a different amino acid sequence than the protease in the above-cited patent application publication, and that it was an enzyme capable of decomposing gelatin and collagen into large fragments. The present invention was devised by determining the amino acid sequence and base sequence corresponding to this enzyme.

DESCRIPTION OF THE INVENTION

The present invention is as follows:

(1) A protease having the properties stated in (i) and (ii) below:

(i) a molecular weight of 21,000±1,000 (by SDS-PAGE) and (ii) specific protease activity cutting the Gly-Phe site of a peptide or protein comprising amino acid sequence (1) below, cutting the Gly-Phe site of a peptide or protein comprising amino acid sequence (2) below, or cutting the Ser-Leu site of a peptide or protein comprising amino acid sequence (3) below:

Pro-Gln-<u>Gly-Phe</u>-Gln-Gly-Pro       (1, SEQ ID NO:4)

Pro-Ala-<u>Gly-Phe</u>-Ala-Gly-Pro       (2, SEQ ID NO:5)

Gln-Thr-Gln-<u>Ser-Leu</u>-Val-Thr-Pro.  (3, SEQ ID NO:6)

(2) DNA having the base sequence of bases 1 to 816 or the base sequence of bases 253 to 816 in SEQ ID NO: 1 of the Sequence Listing.

(3) DNA hybridizing under stringent conditions with DNA comprised of a base sequence complementary to DNA having the base sequence of bases 1 to 816 or the base sequence of bases 253 to 816 in SEQ ID NO: 1 of the Sequence Listing, and encoding a protein having the specific protease activity stated in (ii) of (1) above.

(4) DNA comprised of a base sequence consisting of the base sequence of bases 1 to 816 or the base sequence of bases 253 to 816 in the base sequence of SEQ ID NO: 1 in the Sequence Listing with the deletion, substitution, and/or addition of one or more bases, and coding for a protein having the specific protease activity described in (1) above.

(5) A protein having the amino acid sequence given by SEQ ID NO: 2 or SEQ ID NO: 3 in the Sequence Listing.

(6) A protein comprised of the amino acid sequence given in SEQ ID NO: 2 or 3 of the Sequence Listing with the deletion, substitution, and/or addition of one or more amino acids, and having the specific protease activity described in (1) above.

(7) A protein comprised of an amino acid sequence having not less than 70 percent homology with the amino acid sequence of SEQ ID NO: 2 or 3 of the Sequence Listing, and having the specific protease activity described in (1) above.

(8) DNA encoding the amino acid sequence of any one of the proteins of (5) to (7) above.

(9) A recombinant vector comprising the DNA described in any one of (2) to (4) or in (8).

(10) A transformant comprising the recombinant vector of (9).

(11) A method for manufacturing protease comprising culturing the transformant described in (10) and collecting protein having the specific protease activity described in (1).

BEST MODE OF IMPLEMENTING THE INVENTION

Protease

The protease of the present invention has the properties given in (i) and (ii) below:

(i) a molecular weight of 21,000±1,000 (by SDS-PAGE), and (ii) specific protease activity cutting the Gly-Phe site of a peptide or protein comprising amino acid sequence (1) below, cutting the Gly-Phe site of a peptide or protein comprising amino acid sequence (2) below, or cutting the Ser-Leu site of a peptide or protein comprising amino acid sequence (3) below:

```
Pro-Gln-Gly-Phe-Gln-Gly-Pro        (1, SEQ ID NO:4)

Pro-Ala-Gly-Phe-Ala-Gly-Pro        (2, SEQ ID NO:5)

Gln-Thr-Gln-Ser-Leu-Val-Thr-Pro.   (3, SEQ ID NO:6)
```

The protease of the present invention has specific protease activity cutting a peptide or protein comprising any of the amino acid sequences of (1) to (3) above at the above-stated sites. The protease of the present invention refers to an enzyme having the above-stated cutting activity (specific protease activity). When a peptide or protein contains two or more of the amino acid sequences of (1) to (3) above, the protease of the present invention cuts them all.

The method of preparing the protease of the present invention will be described.

The protease can be obtained by inoculating *Aureobacterium* sp. MIM-CG-9535-1 (FERM P-15326) onto a medium, culturing the bacterium by the usual method, and collecting the protease from the culture product obtained. However, the protease is collected from the culture product based on the specific protease activity of the protease of the present invention, that is, based on cutting specificity at the amino acid sites stated in (ii) above. This will be described further below.

A common microbe medium permitting growth of the specific bacterium can be used to culture the above-stated bacteria; the medium is not specifically limited. A utilizable nitrogen source, carbon source, and inorganic salts are desirably added to the medium in suitable quantities.

The nitrogen source, carbon source, and inorganic salts are not specifically limited. Examples of nitrogen sources are: meat extract, yeast extract, and peptone. Examples of carbon sources are glucose, fructose, sucrose, and glycerin. Examples of inorganic salts are disodium hydrogenphosphate, potassium dihydrogenphosphate, magnesium sulfate, calcium chloride, iron sulfate, and zinc sulfate.

The pH of the medium is desirably about 6 to 7. Culturing is desirably conducted at a temperature of 28 to 30° C. for 20 to 48 hours with shaking.

The collection and purification of the target substance protease from the culture product is conducted based on the specific protease activity—that is, cutting activity—of the protease of the present invention at the amino acid sites indicated in (ii) above.

Specifically, the bacterial mass is separated from the culture product by centrifugation, filtration, or the like, the culture filtrate is concentrated by the usual separation means, such as ammonium sulfate precipitation or with an ultrafiltration membrane, and the concentrate is purified by column chromatography or the like. However, in the course of purification, only the fraction having cutting activity at the amino acid sites indicated in (ii) above is recovered.

In the above-cited patent application publication, the fraction having azocol activity is recovered in the course of protease purification (Paragraph 0028). Further, azocol activity is employed to verify enzyme activity.

Investigation by the present inventors revealed some overlap of fractions having azocol activity and the fraction having cutting activity at the amino acid sites indicated in (ii) above. In the manufacturing of the protease of the present invention, the fraction having cutting activity at the amino acid sites indicated in (ii) above that is recovered also has azocol activity. However, the fractions having azocol activity contain the fraction having cutting activity at the amino acid sites indicated by (ii) above and fractions not having this cutting activity. The protease described in the above-cited patent application publication is a protein that is recovered from nearly all fractions having azocol activity.

Figure 1:
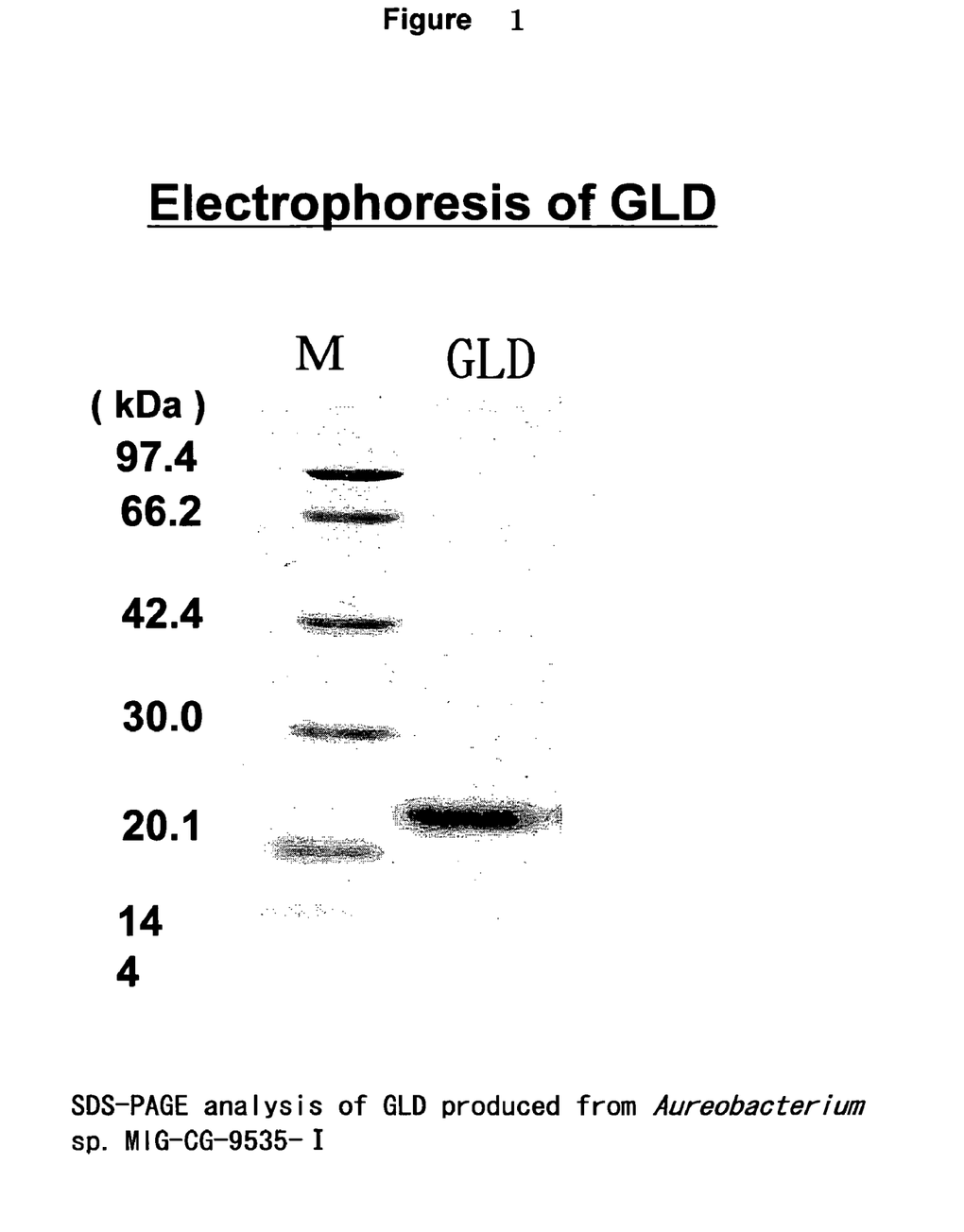
FIG. 1 shows the results of SDS-PAGE electrophoresis of the protein (protease) of the present invention.

As will be clear from the protein SDS-PAGE electrophoresis results of FIG. 1, the protein of the present invention is comprised of a single component having a molecular weight of 21,000±1,000. By contrast, the protein-degrading enzyme for which SDS-PAGE electrophoresis results are given in FIG. 6 of the above-cited patent application publication has a molecular weight of 23,000±2,000; the two are clearly distinct substances. Accordingly, the protein-degrading enzyme described in the above-cited patent application publication is presumed to be a mixture of multiple proteins including the protease of the present invention. However, as set forth further below, the substrate specificity of the protein-degrading enzyme described in the above-cited patent application publication and the protease of the present invention are completely different. Thus, even though the protease of the present invention is contained in the protein-degrading enzyme described in the above-cited patent application publication, the quantity is extremely low and the characteristics thereof are thought to be essentially unknown.

The cutting activity at the amino acid cites indicated in (ii) above (specific protease activity) are measured by the following method.

Fluorescence-labeled peptides having the amino acid sequences denoted by (1) to (3) below are synthesized by the usual methods. Specifically, a fluorescent substance is attached as label on one side of the cutting site of a peptide having one of the amino acid sequences listed below, and a light-extinguishing substance is attached on the other side. Only when the labeled peptide has been cleaved is florescence detected. No fluorescence is detected even when employed as substrate for an enzyme not having cutting activity on the amino acid sequences given below. The substances used to label the peptide are not specifically limited other than that they be fluorescent and light-extinguishing substances. For example, N-methylanthranic acid can be employed as the fluorescent substance, and a dinitrophenyl group can be employed as the light-extinguishing substance.

Pro-Gln-<u>Gly-Phe</u>-Gln-Gly-Pro    (1, SEQ ID NO:4)

Pro-Ala-<u>Gly-Phe</u>-Ala-Gly-Pro    (2, SEQ ID NO:5)

Gln-Thr-Gln-<u>Ser-Leu</u>-Val-Thr-Pro.   (3, SEQ ID NO:6)

To determine specific protease activity in the present invention, a fluorescence-labeled synthetic peptide, obtained by labeling a peptide having one of the amino acid sequences denoted by (1) to (3) above with N-methylanthranic acid on one end and labeling the other end thereof with a dinitrophenyl group, is employed as substrate and incubated with a prescribed quantity of enzyme for a prescribed period in the dark. Subsequently, the product is separated by reverse-phase chromatography and the fluorescent intensity of the separated product is measured to determine cutting activity.

For reference, the degradation activity of the substrate Pro-Gln-Gly-Ile-Ala-Gly-Gln (SEQ ID NO: 7) that can be degraded by the enzyme described in the above-cited patent application publication (Patent Application Publication No. 2000-102381) can be similarly measured.

The cutting activities of the enzyme (protease) of the present invention and the enzyme described in the above-cited patent application publication have been organized into Table 1 below.

TABLE 1

| Protease cutting activity (degradation of synthetic substrate) | | |
|---|---|---|
| Amino acid sequence of synthetic substrate | Enzyme of the present invention | Enzyme of patent application publication |
| Gly-Pro-Ala-Gly-↓-Phe-Ala-Gly-Pro (SEQ ID NO:8) | (○) Degrades | (X) Does not degrade |
| Gly-Pro-Gln-Gly-↓-Phe-Gln-Gly-Pro (SEQ ID NO:9) | (○) Degrades | (X) Does not degrade |
| Gln-Thr-Gln-Ser-↓-Leu-Val-Thr-Pro (SEQ ID NO:6) | (○) Degrades | (X) Does not degrade |
| Pro-Gln-Gly-↓-Ile-Ala-Gly-Gln (SEQ ID NO:7) | (X) Does not degrade | (○) Degrades |

Note:
"↓" denotes the cutting spot.

The peptide or protein serving as substrate must contain one of the amino acid sequences of (1) to (3) above in its entirety in order for the above specific protease activity of the present invention to be exhibited. When even a portion of the above amino acid sequence is missing, the above specific protease activity is not exhibited. However, so long as the entire amino acid sequence of (1) to (3) above is contained, the above specific protease activity is exhibited even if an amino acid is added. Thus, although the synthetic substrates corresponding to the amino acid sequences of (1) and (2) above comprise a Gly on the N terminal, the specific protease activity is exhibited whether or not this Gly is present.

The following table gives the results of an examination conducted with fluorescence-labeled synthetic peptides obtained by changing the sequence of the peptide chain in the amino acid sequence of (1) to determine the amino acid sequence required for exhibition of specific protease activity. Amino acids in Table 2 are show by single letter cords.

TABLE 2

| Peptide chain | | Present or Absent of Specific degradation activity |
|---|---|---|
| GPAG FAGP | (SEQ ID NO:8) | Present |
| GPAG FAG | (SEQ ID NO:10) | Absent |
| GPAG FA | (SEQ ID NO:11) | Absent |
| GPAG F | (SEQ ID NO:12) | Absent |
| PAG FAGP | (SEQ ID NO:5) | Present |
| AG FAGP | (SEQ ID NO:13) | Absent |
| G FAGP | (SEQ ID NO:14) | Absent |

In addition to the specific protease activity indicated in (ii) above, the protease of the present invention has the following characteristics:
(1) Optimal pH: 5.5 to 7.0
(2) Optimal temperature: 37 to 40° C.
(3) Enzyme inhibition: Given in Table 3 below.

TABLE 3

| Name of inhibitor | Concentration mM | Residual activity (%) |
|---|---|---|
| No addition | 0 | 100 |
| o-Phenanthroline | 2 | 0 |
| EDTA | 10 | 93 |
| EGTA | 10 | 68 |
| L-Cys | 20 | 0 |
| 2-ME | 20 | 73 |
| N-Ethylmaleimide | 20 | 79 |
| Antipain | 0.05 | 94 |
| Leupepsin | 0.05 | 92 |
| E-64 | 0.05 | 95 |
| Phosphoramidon | 0.05 | 91 |
| Trypsin inhibitor | 0.05 | 95 |
| Chymostatin | 0.05 | 85 |
| TCPK | 0.1 | 95 |
| PMSF | 20 | 84 |
| Iodoacetamide | 20 | 77 |

The present invention covers DNA having the base sequence of bases 1 to 816 and the base sequence of bases 253 to 816 in SEQ ID NO: 1. DNA having the base sequence of bases 1 to 816 in SEQ ID NO: 1 encodes preprotease. By contrast, DNA having the base sequence of bases 253 to 816 in SEQ ID NO: 1 encodes the mature protease.

The present invention also covers DNA hybridizing under stringent conditions with DNA comprised of a base sequence complementary to DNA having the base sequence of bases 1 to 816 or the base sequence of bases 253 to 816 of SEQ ID NO: 1, and encoding protein having the specific protease activity indicated by (ii) above.

The above term "hybridizing under stringent conditions" means the base sequence of DNA obtained by the colony hybridization method, plaque hybridization method, or southern blot hybridization method using DNA as probe. For example, hybridization is conducted at 65° C. in the presence of 0.7 to 1.0 M of NaCl using a filter on which DNA derived from a colony or plaque or fragments of such DNA have been immobilized. Next, the filter is washed with a 0.1 to 2×SSC solution (1×SSC solution consists of 150 mM of sodium chloride and 15 mM of sodium citrate) at 65° C. to identify the DNA. Hybridization can be conducted according to the method described in Molecular Cloning, 2$^{nd}$ Ed., or the like.

An example of DNA hybridizing under stringent conditions is DNA having homology with the DNA employed as probe, which is greater than a certain level. For example, this is DNA having homology of greater than or equal to 70 percent, desirably greater than or equal to 80 percent, preferably greater than or equal to 90 percent, more preferably greater than or equal to 93 percent, still more preferably greater than or equal to 95 percent, and most preferably greater than or equal to 98 percent.

Whether or not a protein has the specific protease activity indicated in (ii) above can be measured as set forth above with a fluorescence-labeled synthetic peptide.

The present invention further covers DNA comprised of a base sequence consisting of the base sequence of bases 1 to 816 or bases 253 to 816 of SEQ ID NO: 1 with the deletion, substitution, and/or addition of one or more bases, and encoding proteins having the specific protease activity indicated in (ii) above.

Whether or not a protein has the specific protease activity indicated in (ii) above can be measured as set forth above.

The range of "one or more" in "a base sequence ... with the deletion, substitution, and/or addition of one or more bases" referred to in the present Specification is not specifically limited; examples of this range are from 1 to 40, desirably from 1 to 30, preferably from 1 to 20, more preferably from 1 to 10, still more preferably from 1 to 5, and particularly preferably from 1 to 3.

The method of obtaining the DNA of the present invention is not specifically limited. Based on information on the base sequence of SEQ ID NO: 1 in the Sequence Listing of the present Specification, a suitable probe or primer is prepared, and this is then used to screen a cDNA library of various microbes, particularly protease-producing bacteria of the genus *Microbacterium*, to isolate the DNA of the present invention. As set forth above, since we have lumped the genus *Aureobacterium* together with the genus *Microbacterium*, the DNA of the present invention can also be isolated by screening a cDNA library of protease-producing bacteria belonging to the genus *Aureobacterium*. A cDNA library can be prepared by the usual methods from cells expressing the DNA of the present invention.

The DNA of the present invention can be obtained by PCR. A chromosomal DNA library or cDNA library of the above protease-producing bacteria is employed as template and PCR is conducted with a pair of primers designed to permit amplification of the base sequence of SEQ ID NO: 1. The PCR conditions can be suitably set. For example, 30 cycles of a reaction process consisting of 30 sec at 94° C. (denaturation), 30 sec to 1 min at 55° C. (annealing), and 2 min at 72° C. (extension) are conducted, after which the product is reacted for 7 min at 72° C. Next, the amplified DNA fragments can be cloned using a suitable, amplifiable vector in a host such as *E. coli*.

The preparation of the above probe or primer, the construction of a cDNA library, the screening of the cDNA library, and the cloning of the target gene are known to those skilled in the art. For example, they can be conducted by the methods described in Molecular Cloning: A Laboratory Manual, 2$^{nd}$ Ed., Cold Spring Harbor Laboratory, Cold Spring Harbor, N.Y., 1989 (abbreviated hereinafter to "Molecular Cloning, 2$^{nd}$ Ed.") and Current Protocols in Molecular Biology, Supplements 1 to 38, John Wiley & Sons (1987 to 1997) (abbreviated hereinafter to "Current Protocols In Molecular Biology").

The present invention covers proteins having the amino acid sequences of SEQ ID NOS: 2 and 3. The protein having the amino acid sequence of Seq. ID No. 2 comprises 272 amino acids and is a precursor containing the mature protein (85 to 272). By contrast, the protein (188 amino acids) having the amino acid sequence of SEQ ID NO: 3 is the mature protein.

The present invention further covers proteins having the amino acid sequences of SEQ ID NO: 2 or 3 with one or more amino acid deletions, substitutions, and/or additions and having the specific protease activity indicated in (ii) above.

Whether or not a protein has the specific protease activity indicated by (ii) above can be measured as set forth above.

The range of "one or more" in "the amino acid sequence . . . with the deletion, substitution, and/or addition of one or more amino acids" referred to in the present Specification is not specifically limited; examples of this range are from 1 to 20, desirably from 1 to 10, preferably from 1 to 7, more preferably from 1 to 5, and particularly preferably from 1 to 3.

The present invention covers proteins having an amino acid sequence with greater than or equal to 70 percent homology with the amino acid sequence described in SEQ ID NOS: 2 and 3 of the Sequence Listing and having the specific protease activity indicated in (ii) above.

In the present invention, the "homology" in "an amino acid sequence with greater than or equal to 70 percent homology with the amino acid sequence described in SEQ ID NOS: 2 and 3 of the Sequence Listing" is not specifically limited other than that it be greater than or equal to 70 percent. However, it is desirably greater than or equal to 80 percent, preferably greater than or equal to 85 percent, more preferably greater than or equal to 90 percent, and particularly preferably greater than or equal to 95 percent.

The method of obtaining the protein of the present invention is not specifically limited. The protein can be synthesized chemically or produced by gene recombination techniques.

When producing a recombinant protein, the gene (DNA) encoding a protein described above in the present Specification is first obtained. This DNA can then be introduced into a suitable expression system to produce the protein of the present invention. The expression of a protein in an expression system is described further below in the present Specification.

The present invention further covers DNA encoding the amino acid sequence of the above protein. This DNA can be produced by any method known to those skilled in the art, such as chemical synthesis, genetic engineering methods, and induced mutation based on the amino acid sequence and base sequence information given in SEQ ID NOS: 2 and 3 in the Sequence Listing.

For example, DNA having the base sequence given in Seq. ID No. 1 of the Sequence Listing can be produced by methods employing contact with drugs serving as mutagens, methods employing irradiation with UV radiation, and genetic engineering techniques. Site-specific induced mutation, a genetic engineering technique, is useful as a method of introducing a specific mutation at a specific position. It can be conducted according to the methods described in Molecular Cloning, 2$^{nd}$ Ed.; Current Protocols in Molecular Biology; and the like.

The present invention also covers a recombinant vector containing the above DNA of the present invention.

The DNA of the present invention can be inserted into a suitable vector for use. The type of vector employed in the present invention is not specifically limited. For example, a self-replicating vector (such as a plasmid) may be employed. Alternatively, a vector that is incorporated into the genome of a host cell and replicated along with the recombinant chromosome in the course of introduction into a host cell may be employed.

The vector employed in the present invention is desirably an expression vector. In an expression vector, the gene of the present invention is functionally connected to the elements (such as promoters) required for transcription. A promoter is a DNA sequence indicating transcription activity in a host cell, and can be suitably selected based on the type of host cell.

Examples of promoters capable of operating in bacterial cells are the promoters of the *Bacillus stearothermophilus* matogenic amylase gene, *Bacillus lichenformis* alpha-amylase gene, *Bacillus amyloliquefaciens* BAN amylase gene, *Bacillus subtilis* alkaline protease gene, and *Bacillus pumilus* xylosidase gene; phage lambda $P_R$ and $P_L$ promoters; and lac, trp, and tac promoters of *E. coli*.

As necessary, the gene of the present invention can be functionally linked to a suitable terminator. The recombinant vector of the present invention may also have elements such as a polyadenylation signal (for example, one derived from SV40 or the adenovirus 5E1b region) or a transcription enhancer sequence (for example, the SV40 enhancer).

The recombinant vector of the present invention may also be equipped with a DNA sequence permitting replication of the vector in a host cell, one example of which is an SV40 replication start codon (when the host cell is a mammal cell).

The recombinant vector of the present invention may also contain a selection marker. Examples of selection markers are dihydrofolic acid reductase (DHFR), *Schizosaccharomyces pombe* TPI gene, and other genes the complement of which is lacking in the host cell; and genes imparting resistance to drugs such as ampicillin, kanamycin, tetracycline, chloramphenicol, neomycin and hygromycin. Methods of linking the gene of the present invention, a promoter, and if desired, a terminator and/or secretion signal sequence, and introducing them into a suitable vector are widely known to those skilled in the art.

The vector constituting the recombinant vector of the present invention is not specifically limited other than that it permits expression in a host; the vector can be suitably selected based on the relation to the host.

The present invention covers transformants containing the above-described recombinant vector of the present invention.

The DNA or recombinant vector of the present invention can be introduced into a suitable host to prepare a transformant.

The host cell into which the gene or recombinant vector of the present invention is introduced can be any cell capable of expressing the gene of the present invention; examples are bacteria, yeasts, fungi, and higher eukaryotes.

The host constituting the transformant of the present invention is not specifically limited. Examples of bacterial cells are gram-positive bacteria such as *Bacillus* and *Streptomyces*, and gram-negative bacteria such as *E. coli*. The transformation of these bacteria can be accomplished by the protoplast method, or using competent cells by known methods.

However, from the perspective of efficiently producing the protein (protease) of the present invention, the host constituting the transformant of the present invention is desirably a microbe belonging to the genus *Brevibacillus*. Examples of microbes belonging to the genus *Brevibacillus* are: *B. brevis, B. choshinensis, B. formosus, B. parabrevis, B. reuszeri, B. agri, B. centrosporus, B. borstelensis, B. laterosporus*, and *B. thermoruber*.

Yeast cells are a further example of bacteria cells. Examples of yeast cells are cells belonging to *Saccharomyces* and *Schizosaccharomyces*. Specific examples are *Saccharomyces cerevisiae* and *Saccharomyces kluyveri*. The recombinant vector can be introduced into a host cell by, for example, electroporation, the spheroblast method, and the lithium acetate method.

Examples of fungi cells are filamentous cells belonging to genera such as *Aspergillus, Neurospora, Fusarium*, and *Trichoderma*. When employing a filamentous cell as host cell, transformation can be conducted by incorporating the DNA structure into the chromosome of the host to obtain a recombinant host cell. The DNA structure can be incorporated into the host chromosome by known methods; for example, by homologous recombination or heterologous recombination.

The present invention covers a method for manufacturing protease by culturing the above-described transformant of the present invention and collecting the protein having the specific protease activity indicated in (ii) above.

The method of cultivating the transformant of the present invention can be suitably selected based on the type of host employed.

The medium employed to culture the transformant is not specifically limited other than that it be a medium employed for common microbes that is capable of growing the particular transformant. A utilizable nitrogen source, carbon source, and inorganic salts are desirably added to the medium in suitable quantities.

The nitrogen source, carbon source, and inorganic salts are not specifically limited. Examples of nitrogen sources are: meat extract, yeast extract, and peptone. Examples of carbon sources are glucose, fructose, sucrose, and glycerin. Examples of inorganic salts are disodium hydrogenphosphate, potassium dihydrogenphosphate, magnesium sulfate, calcium chloride, iron sulfate, and zinc sulfate.

The pH of the medium and the culture temperature are determined based on the type of host. When the host is a microbe belonging to the genus *Bacillus*, the pH can be 7.5 to 10 and the culture temperature can be about 30° C.

The culture period can be suitably determined. For example, culturing can be conducted for 20 to 48 hours with shaking.

When expressed within a cell in a dissolved state, the protein of the present invention is obtained following the conclusion of culturing by recovering the cells by centrifugal separation, suspending the cell mass in an aqueous buffer solution, and rupturing the cells with an ultrasonic disintegrator to obtain a cell-free extract. The cell-free extract is subjected to centrifugal separation and the supernatant is subjected to the usual protein isolation and purification methods. These include solvent extraction; salting out with ammonium sulfate etc; desalting; precipitation from organic solvents; anionic exchange chromatography using resins such as diethylaminoethyl (DEAE) sepharose; cationic exchange chromatography employing resins such as S-Sepharose FF (made by Pharmacia Corp.); hydrophobic chromatography employing resins such as butyl sepharose and phenyl sepharose; gel filtration methods employing molecular sieves; affinity chromatography; chromatofocusing methods; and electrophoretic methods such as isoelectric focusing, which may be employed singly or in combination to obtain a pure preparation.

The target substance protease is recovered from the culture product and purified based on the specific activity of the protease of the present invention; that is, based on the cutting activity at the amino acid sites indicated in (ii) above. This cutting activity is measured in the same manner as described for the method of preparing the protease of the present invention.

EMBODIMENTS

The present invention is described more specifically below through embodiments.

Embodiment 1

Manufacturing the Protease of the Present Invention

*Aureobacterium* sp. MIM-CG-9535-1 (FERM P-15326) was aerobically cultured for 16 to 24 hours at 28° C. in growth medium (Table 4). The bacterial mass was centrifugally separated after culturing, ammonium sulfate was added to the culture solution obtained, and the 55 percent saturation precipitation fraction was collected by centrifugation. This precipitate was dissolved in 20 mM Tris-HCl (pH 7.5), 8 mM calcium chloride, and 0.1 M ammonium sulfate buffer solution. After adjusting the buffer solution to a 0.8 M ammonium sulfate concentration, centrifugation was conducted and the supernatant was retained.

TABLE 4

| Culture medium component | Quantity incorporated |
|---|---|
| Polypeptone | 5 g |
| Yeast extract | 5 g |
| Sodium chloride | 10 g |
| Glucose | 10 g |
| $Na_2HPO_4$ | 7.04 g |
| $K_2HPO_4$ | 4.14 g |
| Hunter inorganic salt solution | 40 mL |
| Water | 1 L | pH 6.8

This supernatant was purified by the following method.

Purification method (purification by ammonium sulfate)

Buffer A: 20 mM Tris-HCl (pH 7.4)•1 mM $CaCl_2$ •0.9 M $AmSO_4$

Buffer B: 20 mM Tris-HCl (pH 7.4)•1 mM $CaCl_2$ •0.1 M $AmSO_4$ i) Culture concentrate that had been kept in frozen storage at −20° C. was thawed out.

ii) An ion chromatogram (Butyl-TOYOPEARL) was prepared and equilibrated with Buffer A.

iii) $AmSO_4$ was added to render electrical conductivity of the thawed culture solution the same as that of Buffer A. Following thorough stirring, the pH was adjusted to 7.4, centrifugation was conducted, and the supernatant was collected.

iv) The supernatant was applied to a column and washed upon completion of the application.

v) Following washing, the product was eluted with Buffers A and B. The activity and protein level of the fractions thus obtained were tested, and the individual fractions were subjected to electrophoresis to obtain a pooled fraction.

vi) The pooled fraction was concentrated with a membrane with a molecular weight of 10,000 and subjected to dialysis.

vii) The product was dissolved in 5 mM MES (pH 5.5) 150 mM $NaCl_2$•5 mM $CaCl_2$ to complete purification.

Measurement of Molecular Weight

Molecular weight was measured in the following manner. The above purified enzyme was treated with SDS and 2-mercaptoethanol (reducing agents) and subjected to electrophoresis. The molecular weight was calculated from molecular weight markers and the migration distance of the sample. The results are given in FIG. 1.

Measurement of Cutting Activity (Specific Protease Activity)

Cutting activity (specific protease activity) was measured as follows.

Nma/Dnp florescence-labeled peptides (excitation wavelength 340 nm, fluorescence wavelength 440 nm) having the amino acid sequences of (1) to (3) below labeled on one end with N-methylanthranic acid and on the other end with a dinitrophenyl group were synthesized with a peptide synthesizer by the usual method.

```
Nma-Gly-Pro-Gln-Gly-Phe-Gln-Gly-    (1, SEQ ID NO:15)
Pro-Lys-(DNP)r-NH₂

Nma-Gly-Pro-Ala-Gly-Phe-Ala-Gly-    (2, SEQ ID NO:16)
Pro-Lys-(DNP)r-NH₂

Nma-Thr-Gln-Ser-Leu-Val-Thr-Pro-    (3, SEQ ID NO:17)
Lys-(DNP)r-NH₂
```

Nma: N-methylanthranic acid

DNP: Dinitrophenyl group

Employing as substrate one of the fluorescence-labeled synthetic peptides obtained, cutting activity was measured under the following conditions.

A 100 microgram quantity of fluorescence-labeled synthetic peptide was adjusted to 0.2 mg/mL with 10 mM Tris buffer solution, 1 microgram of the above protease of the present invention was added, and the mixture was incubated for 10 min at 37° C. in the dark. The enzyme reaction solution obtained was subjected to reverse-phase HPLC using TSK gel ODS 80T (Tohso Corp.) from 0.1 percent TFA to 80 percent acetonitrile-0.1 percent TFA at a flow rate of 1 mL/min and a gradient of 40 min to separate the degraded peptides. Employing A215 and a fluorescence spectrometer for high-performance liquid chromatography made by Shimatsu Corp., fluorescent intensity was measured at an excitation wavelength of 340 nm and a fluorescence wavelength of 440 nm.

The results are given in Table 1.

For comparison, the cutting activity of the enzyme described in the above-cited patent application publication (Japanese Patent Application Publication No. 2000-102381) was measured under identical conditions. The results are given in Table 1.

Fluorescence-labeled synthetic peptides were obtained in the same manner as set forth above for the Pro-Gln-Gly-Ile-Ala-Gly-Gln (SEQ ID NO: 7) for which the enzyme of the above-cited patent application publication exhibited cutting activity, and in the same manner as above, the cutting activity of the enzyme of the present invention and the enzyme described in the above-cited patent application publication were measured. The results are given in Table 1.

The structure of the peptide chain was varied in the amino acid sequence of (1) above, fluorescence-labeled synthetic peptides were synthesized in the same manner as above, and cutting activity was measured in the same manner as above to verify the amino acids required for the above specific degradation activity. The results are given in Table 2.

The following characteristics of the enzyme (protease) of the present invention obtained as set forth above were measured as follows.

(1) Temperature Stability and Optimal Temperature of the Enzyme i) Temperature Stability The enzyme was left standing for one hour at various temperatures of from 0 to 60° C. and subsequently reacted with a synthetic substrate for 30 min at 37° C. Enzyme activity was then measured.

ii) Optimal Temperature

A synthetic substrate solution and enzyme solution were reacted for 30 min at various temperatures from 0 to 60° C. and the enzymatic activity was measured.

(2) pH Stability and Optimal pH of the Enzyme i) pH Stability

Buffer solutions were prepared at pH increments of 0.5 over the pH range of 3.0 to 5.0 with acetic acid and sodium acetate buffer solution and over the pH range of 5.0 to 9.0 with MES-HEPES-boric acid buffer solution. Enzyme was added to each of the buffer solutions and the mixture was ice cooled for one hour with light stirring. Subsequently, synthetic substrate solution was added and the residual enzymatic activity was measured.

ii) Optimal pH

Synthetic substrate solutions were prepared with each of the above-described buffer solutions, enzyme solution was added, and the enzymatic activity was measured.

(3) Enzyme Inhibiting Effect

Reagents in the form of o-phenanthroline, EDTA, EGTA, L-cysteine, 2-mercaptoethanol, N-ethylmaleimide, antipain, leupepsin, E-64, phosphoramidon, trypsin inhibitor, chymostatin, TCPK, PMSF, and iodoacetamide were employed as inhibitors.

Each of the reagents was mixed with the synthetic substrate after which the enzyme was added. The degradation reaction was conducted for 30 min at 37° C. and the enzymatic activity was measured. Adopting the case where no inhibitor was added as 100 percent, the relative residual enzymatic activity was calculated.

The results of the above were as follows.

(1) Temperature stability: The enzyme itself was thermally weak, being nearly deactivated at 40° C. and above and with residual activity being only about half at 30° C.

Optimal temperature: 37 to 40° C.

(2) pH stability: There was stability over a range of pH 3 to 9.

Optimal pH: 5.5 to 7.0

(3) Enzyme inhibition: Given in Table 3 above.

The enzyme (protease) of the present invention obtained as set forth above was DNA sequenced and amino acid sequenced.

DNA Sequencing Method

The base sequence was determined by sequence PCR using forward/reverse primer and a DYEnamic™ ET Terminator Sequencing Kit (Amersham). The sequence was analyzed with DNASYS software and Genetyx-Mac-10.0. The results are given in SEQ ID NO: 1 of the Sequence Listing.

Amino Acid Sequencing Method

The N-terminal amino acid sequence was analyzed with a liquid-phase protein sequencer and the internal amino acid sequence was similarly analyzed for the protease degradation products. Based on the sequences obtained, oligonucleotide primers were prepared and amplified by PCR. The results are given as SEQ ID NOS: 2 and 3 in the Sequence Listing.

The invention claimed is:

1. An isolated or purified polypeptide which has a proteolytic activity of cutting at a Gly-Phe site or a Ser-Leu site of a peptide or protein, and which is selected from the group consisting of:
   (a) a polypeptide which is encoded by a polynucleotide having at least 95% sequence identity to nucleotides 253-816 of SEQ ID NO: 1,
   (b) a polypeptide which is encoded by a polynucleotide that hybridizes to the full complement of nucleotides 1-816 or to the full complement of nucleotides 253-816 of SEQ ID NO: 1 under stringent conditions defined by washing at 65° C. in 0.5×SSC, and
   (c) a polypeptide which comprises the amino acid sequence of SEQ ID NO: 2 or 3.

2. The polypeptide of claim 1, which has a proteolytic activity of cutting at a Gly-Phe site of an amino acid sequence.

3. The polypeptide of claim 1, which has a proteolytic activity of cutting at a Ser-Leu site of an amino acid sequence.

4. The polypeptide of claim 1, which has a molecular weight of 21,000±1,000 as determined by SDS-PAGE.

5. The polypeptide of claim 1, which is encoded by a polynucleotide at least 95% identical to nucleotides 253-816 of SEQ ID NO: 1.

6. The polypeptide of claim 1, which is encoded by a polynucleotide that hybridizes to the full complement of nucleotides 1-816 or nucleotides 253-816 of SEQ ID NO: 1 under stringent conditions defined by washing at 65° C. in 0.5×SSC.

7. A composition comprising the polypeptide of claim 1 and a carrier optionally containing a buffer.

8. A method of cutting a peptide or protein comprising:
   contacting said peptide or protein comprising a Ser-Leu site or a Gly-Phe site with the polypeptide of claim 1.

9. The method of claim 8, wherein said peptide or protein comprises a Ser-Leu site.

10. The method of claim 8, wherein said peptide or protein comprises a Gly-Phe site.

11. The isolated or purified polypeptide of claim 1 which comprises the amino acid sequence of SEQ ID NO: 2 or 3.

12. The isolated or purified polypeptide of claim 1, which consists of the amino acid sequence of SEQ ID NO: 3.

* * * * *